United States Patent
Qi et al.

(10) Patent No.: US 12,172,007 B2
(45) Date of Patent: Dec. 24, 2024

(54) COMBINATION THERAPY OF ELECTRIC FIELDS AND AN ADDITIONAL TREATMENT FOR CANCER AND IMAGING

(71) Applicant: University of Cincinnati, Cincinnati, OH (US)

(72) Inventors: Xiaoyang Qi, Cincinnati, OH (US); Ahmet Kaynak, Cincinnati, OH (US); Daria Narmoneva, Cincinnati, OH (US); Andrei Kogan, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 954 days.

(21) Appl. No.: 17/071,475

(22) Filed: Oct. 15, 2020

(65) Prior Publication Data

US 2021/0106819 A1   Apr. 15, 2021

Related U.S. Application Data

(60) Provisional application No. 62/915,035, filed on Oct. 15, 2019.

(51) Int. Cl.
| | |
|---|---|
| *A61N 1/20* | (2006.01) |
| *A61K 31/196* | (2006.01) |
| *A61K 31/495* | (2006.01) |
| *A61K 39/395* | (2006.01) |
| *A61K 47/64* | (2017.01) |
| *A61K 49/14* | (2006.01) |
| *A61N 5/10* | (2006.01) |

(52) U.S. Cl.
CPC .............. *A61N 1/20* (2013.01); *A61K 31/196* (2013.01); *A61K 31/495* (2013.01); *A61K 39/39558* (2013.01); *A61K 47/64* (2017.08); *A61K 49/14* (2013.01); *A61N 5/10* (2013.01)

(58) Field of Classification Search
CPC .......... A61N 1/20; A61N 5/10; A61K 31/196; A61K 31/495; A61K 39/39558; A61K 47/64; A61K 49/14; A61K 49/1809; C07K 16/28
See application file for complete search history.

(56) References Cited

U.S. PATENT DOCUMENTS

| | | | | |
|---|---|---|---|---|
| 2005/0043726 | A1* | 2/2005 | McHale | A61N 7/00 977/932 |
| 2019/0298982 | A1* | 10/2019 | Story | A61P 35/00 |

FOREIGN PATENT DOCUMENTS

| | | | |
|---|---|---|---|
| WO | WO 2015200790 | * | 12/2015 |

OTHER PUBLICATIONS

Derose et al., ("Development of Bavituximab, a Vascular Targeting Agent with Immune-Modulating Properties, for Lung Cancer Treatment", Immunotherapy, 3(8):933-944, 2011) (Year: 2011).*

(Continued)

Primary Examiner — Alexei Bykhovski
(74) Attorney, Agent, or Firm — Brent M. Peebles

(57) ABSTRACT

A method of treating cancer is disclosed. The method involves applying one or more direct current electric fields (DC-EFs) to a subject and administering to the subject an additional treatment selected from the group consisting of radiation, an effective amount of one or more chemotherapy agents, SapC-DOPS, anti-phosphatidylserine targeted drugs, and combinations thereof.

11 Claims, 12 Drawing Sheets

(56) References Cited

OTHER PUBLICATIONS

Sulaiman et al (SapC-DOPS nanovesicles induce Smac- and Bax-dependent apoptosis through mitochondrial activation in neuroblastomas, Molecular Cancer (2015) 14:78) (Year: 2015).*

Kaynak, A; Davis, H; Kogan, A; Narmoneva, D; Qi, X; "Electric Field-assisted Phosphatidylserine Exposure Level Alteration in Glioblastoma Cells", Biomedical Engineering, University of Cincinnati, OH; Division of Hematology/Oncology, Department of Internal Medicine, University of Cincinnati Medical Center, OH; Physics Department, University of Cincinnati, OH.

Wojton J, Chu Z, Mathsyaraja H, et al. Systemic delivery of SapC-DOPS has antiangiogenic and antitumor effects against glioblastoma. Molecular therapy : the journal of the American Society of Gene Therapy. 2013;21(8):1517-1525.

Davis HW, Vallabhapurapu SD, Chu Z, et al. Enhanced phosphatidylserine-selective cancer therapy with irradiation and SapC-DOPS nanovesicles. Oncotarget. 2019; 10(8):856-868.

* cited by examiner

COMBINATION THERAPY OF ELECTRIC FIELDS AND AN ADDITIONAL TREATMENT FOR CANCER AND IMAGING

CROSS REFERENCE TO RELATED APPLICATIONS

This application claims priority to U.S. Provisional Application Ser. No. 62/915,035, filed Oct. 15, 2019, which application is hereby incorporated by reference in its entirety.

TECHNICAL FIELD

The present invention relates to methods of imaging and treating cancer using direct current electric fields.

BACKGROUND OF THE INVENTION

Cancer is a major cause of morbidity and mortality globally. In 2012, about 14 million new cancer cases and 8 million deaths occurred worldwide. While there has been significant progress in the diagnosis and treatment of cancer over the last decades, the overall reduction in cancer mortality is still modest. Furthermore, cancer-related cases and deaths are expected to rise to more than 22 million by 2030. Even if current standard treatments such as chemotherapy and radiotherapy are successful, there remains a significant risk of relapse. Major concerns about currently available treatment options are low therapeutic indices (defined as a ratio of the drug concentration at which a drug becomes toxic and the concentration at which the drug is effective) and a broad spectrum of side effects, including toxicity and drug resistance. The lack of specificity of existing therapies toward tumor cells is the main cause of potential toxicity and drug resistance. Drug resistance can be categorized as intrinsic (primary resistance) or acquired (secondary resistance). Intrinsic resistance usually occurs because of genetic variations in tumors and how the individual handles the tumor. Acquired resistance includes various drug resistance mechanisms such as drug detoxification mechanisms, expression of energy-dependent transporters which eject the drugs from the cells before interaction with intracellular targets, or cancer cells acquiring the ability to escape drug-induced apoptosis. Over the last few decades, overall adjuvant and curative cytotoxic chemotherapy has not appreciably improved treatment outcomes for most cancer types. As such, there is a need for new therapeutic options that overcome limitations of current therapies and which reduce cancer-related mortality and morbidity.

Considerable effort in recent years has been devoted to developing novel targeted anti-cancer strategies, such as specific agents that are able to regulate the cell cycle, inhibit cancer cell proliferation and induce apoptosis or autophagy. Still, there is an urgent need to develop alternative therapeutics which specifically act through cancer biomarkers expressed within certain types of tumors in order to enhance the selectivity of chemotherapeutic agents.

SUMMARY OF THE INVENTION

In one embodiment, the present invention is a method of treating cancer in a subject who is in need thereof. The method involves applying one or more direct current electric fields (DC-EFs) to the subject and administering to the subject an additional treatment selected from the group consisting of radiation, an effective amount of one or more chemotherapy agents, Saposin C (SapC) and dioleoylphosphatidylserine (DOPS) (SapC-DOPS), anti-phosphatidylserine targeted drugs, and combinations thereof. In one embodiment, the magnitude of the applied DC-EF is from about 0.1 V/cm to about 100 V/cm. In another embodiment, the magnitude of the applied DC-EF about 75 V/cm.

In one embodiment, the additional treatment comprises a chemotherapy agent. In another embodiment, the chemotherapy agent is selected from the group consisting of temozolamide, vincristine, gemcitabine, nab-paclitaxel, paclitaxel, 5-fluorouracil, oxaliplatin, irinotecan, cisplatin, carboplatin, etoposide, leucovorin, irinotecan, oxaliplatin, lenalidomide, carmustine (BCNU), cyclophosphamide, lomustine (CCNU), methotrexate, procarbazine, and everolimus. In one embodiment, the chemotherapy agent is temozolomide. In another embodiment, the additional treatment comprises a radiotherapy agent. In one embodiment, the radiotherapy agent is lutetium Lu 177 dotatate.

In another embodiment, the magnitude of the applied DC-EF is from about 100 V/cm to about 1,500 V/cm. In one embodiment, the magnitude of the applied DC-EF about 150 V/cm. In another embodiment, the additional treatment comprises SapC-DOPS. In one embodiment, the additional treatment comprises anti-phosphatidylserine targeted drugs. In another embodiment, the anti-phosphatidylserine targeted drugs are selected from the group consisting of Bavituximab, PPS1D1 and combinations thereof.

In another embodiment, the present invention is a method of killing or inhibiting the growth of cancer cells in a target region. The method involves the steps of: a) applying, to the target region, one or more direct current electric fields (DC-EFs), wherein the applied DC-EF has a magnitude from about 75 V/cm to about 150 V/cm; and b) treating the cancer cells with additional treatment selected from the group consisting of radiation, an effective amount of one or more chemotherapy agents, Saposin C (SapC) and dioleoylphosphatidylserine (DOPS) (SapC-DOPS), anti-phosphatidylserine targeted drugs, and combinations thereof. In one embodiment, the applying step and the treating step are performed simultaneously. In one embodiment, the applying step and the treating step are performed at different times.

In one embodiment, the present invention is a method of imaging cancerous cells in a subject. The method involves applying one or more direct current electric fields (DC-EFs) to the subject, then administering to the subject an additional treatment of Saposin C (SapC)-based delivery systems, where the SapC-DOPS comprises one or more contrast agents. Then, the method involves detecting the contrast agents in the subject. In one embodiment, SapC-DOPS nanovesicles are used. In another embodiment, the SapC-DOPS nanovesicles are labeled with far red fluorophore, CellVue Maroon (CVM) for optical imaging. In one embodiment, ultra-small cuperparamagnetic iron oxide (USPIO) or gadolinium chelates (Gd-DTAP-BSA) are encapsulated in SapC-DOPS nanovesicles for use as MRI contrast agents. In another embodiment, the SapC-DOPS combined with Iodine-124 as a contrast agent for in vivo Pet/Spect imaging.

DETAILED DESCRIPTION OF THE INVENTION

Figure 1:
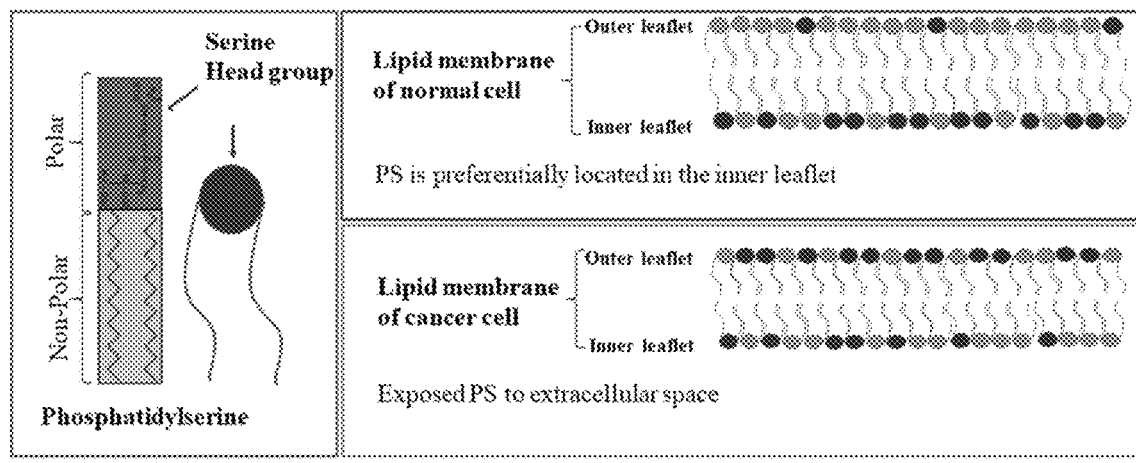
FIG. 1 is a schematic representation of phosphatidylserine and its distribution on normal and cancer cells. The darker circles represent the PS head group.

The details of one or more embodiments of the disclosed subject matter are set forth in this document. Modifications to embodiments described in this document, and other embodiments, will be evident to those of ordinary skill in the art after a study of the information provided herein.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

While the following terms are believed to be well understood by one of ordinary skill in the art, definitions are set forth to facilitate explanation of the disclosed subject matter. Unless defined otherwise, all technical and scientific terms used herein have the same meaning as commonly understood by one of ordinary skill in the art to which the disclosed subject matter belongs.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Generally, the majority of cancer drugs on the market elicit their effects via direct interactions with proteins or DNA. However, as most cellular functions occur in or around membranes, changes in the structure of the membrane or its composition are related to the appropriate functioning of the cells. Therefore, membrane lipids have arisen as alternative molecular targets for multiple therapies since there is increasing evidence for a role of these lipids in the control of various cellular functions and activities of membrane proteins. Membrane lipid therapy is a highly promising approach that has potential for the treatment of number of diseases, including cancer, cardiovascular diseases, metabolic disorders, obesity, inflammation, infections and autoimmune diseases. Of particular interest is the prospect of using phosphatidylserine (PS), a phospholipid commonly found in all cell membranes as an attractive biomarker for anti-cancer therapy.

In one embodiment, the present invention uses a combined biomarker-driven therapy with electric field and PS-targeted drugs to produce improved results. The invention involves the discovery that direct current electric fields can modify the surface PS levels of cancer cells. We have surprisingly found that while a low-DC electric field (e.g. 75 V/cm) results in a significant decrease in the surface PS levels, high-DC electric field (e.g. 150 V/cm) exposure results in the significantly greater surface PS levels for glioblastoma cells. In one embodiment, the present invention uses a high-DC electric field in combination with one or more PS-targeting treatments such as SapC-DOPS to kill cancer cells. In another embodiment, the present invention uses a low-DC electric field in combination with one or more chemotherapeutic drugs such as temozolomide to kill cancer cells. The present invention is a flexible approach to cancer treatment, allowing practitioners to choose a magnitude of electric field that will improve the performance of the chosen course of treatment.

The use of electric fields (EF) is gaining attention in the fight against cancer, yet current modalities are limited to electroporation or low intensity tumor-treating field (TT-Field). Although biomarker-driven cancer therapy has seen growing interest in glioblastoma (GBM) treatment, there is a critical gap between targeting cancer-related biomarkers and enhancing biomarker-matched targeted therapies, for example, by using EF. More importantly, it has been shown in multiple previous studies that increasing a cancer biomarker phosphatidylserine (PS) exposure by using chemo- and radiation-therapy is a logical approach to sensitize GBM cells to PS targeting drugs. However, these combinations have the drawback of potentially harming healthy cells. The present invention involves the surprising discovery that low intensity direct current electric field (LIDC-EF) can be used as a safer method to sensitize GBM cells to the chemotherapeutic drug, temozolomide or PS targeting treatments such as SapC-DOPS.

Figure 6A:
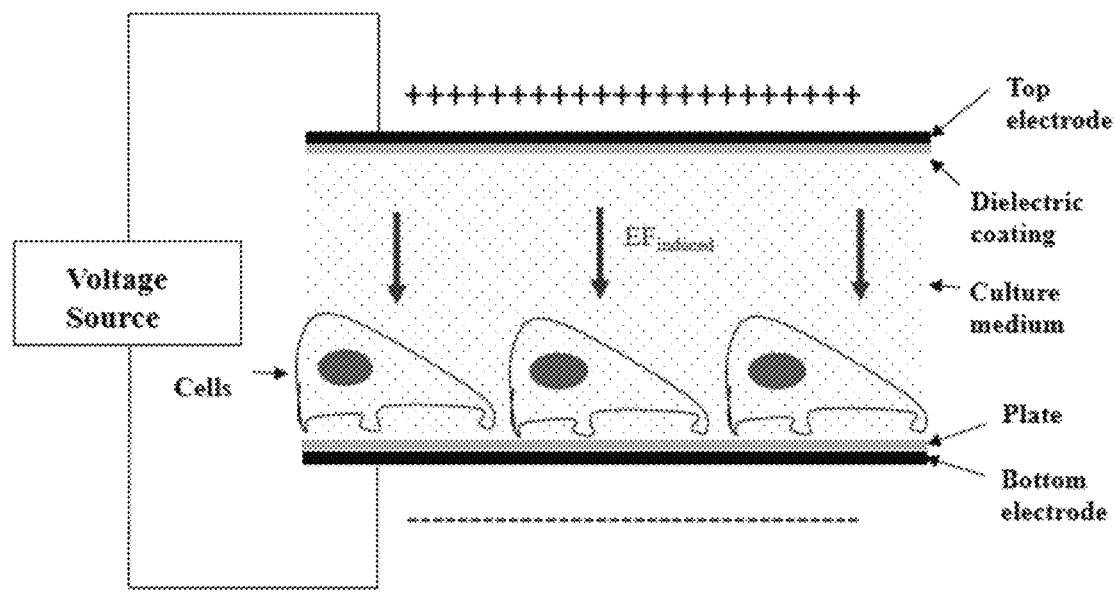
FIG. 6A is a schematic representation of an electric field system.
Figure 6B:
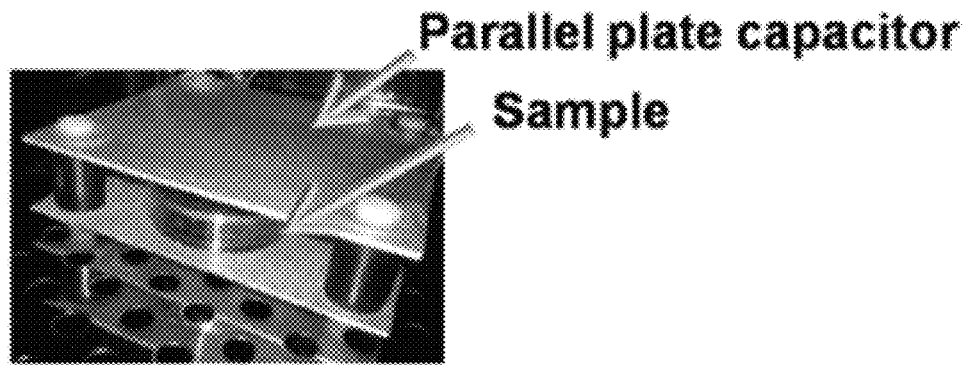
FIG. 6B is a photograph of one embodiment of the present invention showing a system for electrical stimulation of cells using the capacitive coupling method.
Figure 6C:
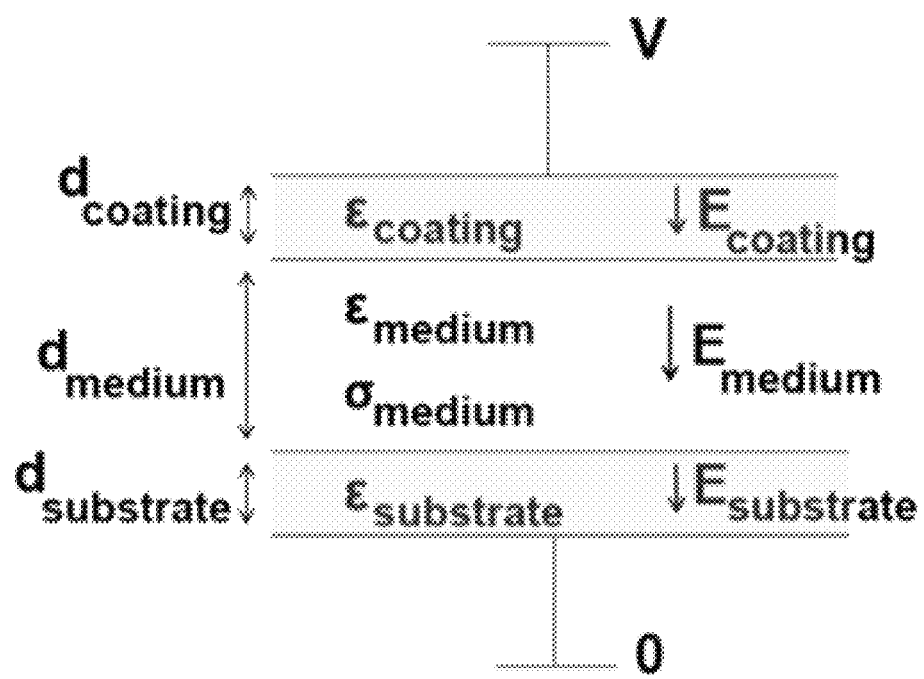
FIG. 6C shows the boundaries and regions of the model shown in 6A and 6B.

In one embodiment, the present invention applies an electric field by a parallel-plate capacitor and the plates of the capacitor are connected to a DC voltage generator. In this embodiment, the electric field device is electrode free, meaning that there are no electrodes touching the medium and cells directly. The electric field is applied through capacitor plates and there is also no direct current flow into the medium. In one embodiment, the magnitude of DC electric field that is applied is in the range from about 75 V/cm (low) to about 150 V/cm (high). In another embodiment, the magnitude of DC electric field that is applied is about 75 V/cm. In yet another embodiment, the magnitude of DC electric field that is applied is about 150 V/cm. A schematic representation of the electric field system device is shown in FIG. 6A. FIG. 6B is a photograph of one embodiment of a system for electrical stimulation of cells using the capacitive coupling method. FIG. 6C shows the boundaries and regions of the model.

Figure 7:
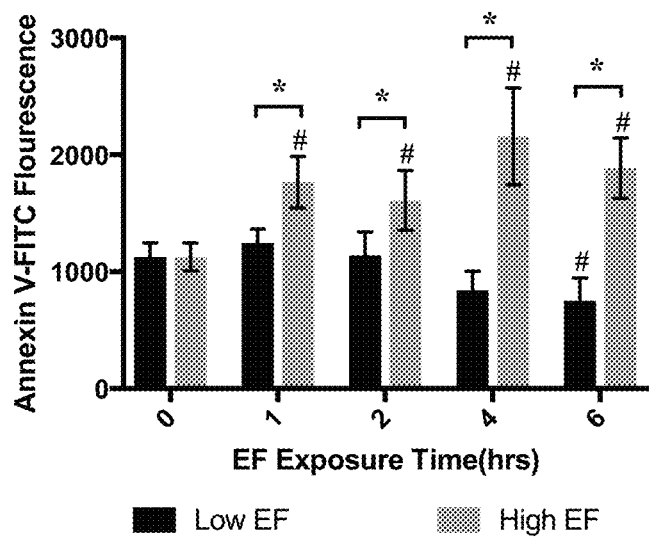
FIG. 7 is a graph showing that a low-DC electric field (75 V/cm) results in a significant decrease in the surface PS levels, while high-DC electric field (150 V/cm) exposure results in the significantly greater surface PS levels in U87ΔEGFR-Luc glioblastoma cells.

We have surprisingly found that applying an electric field plays a role on regulation of PS. Our data demonstrates that while a low-DC electric field (75 V/cm) results in a significant decrease in the surface PS levels, high-DC electric field (150 V/cm) exposure results in the significantly greater surface PS levels in U87ΔEGFR-Luc glioblastoma cells (FIG. 7).

Figure 8:
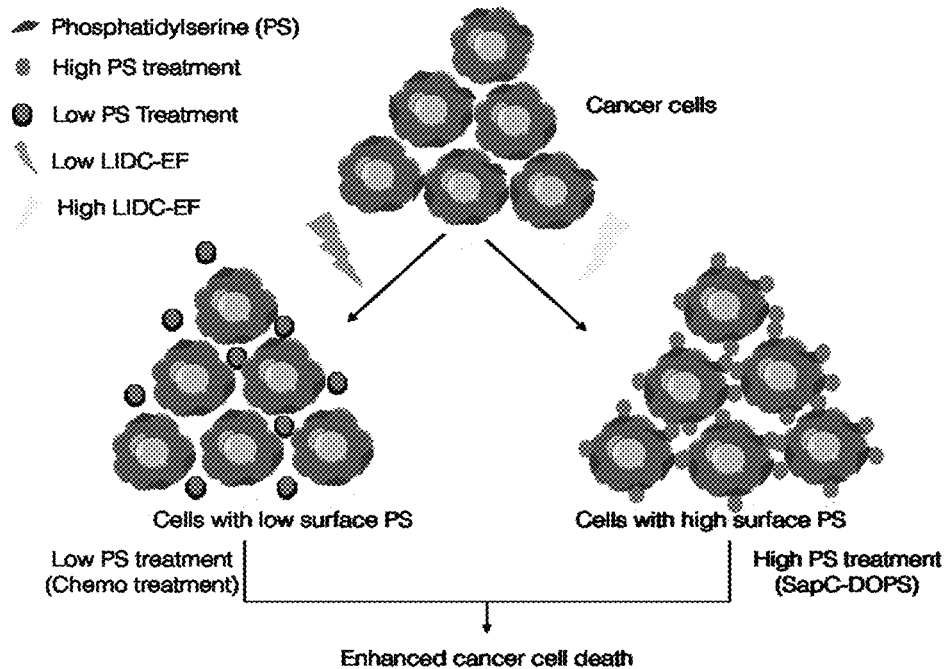
FIG. 8 is an illustration showing how low LIDC-EF (low intensity direct current electric field) mediated PS exposure on glioblastoma (GBM) cells sensitizes the cells to low-PS treatments such as chemotherapy and radiation. It also shows that increasing GBM cells' PS exposure by high LIDC-EF will enhance the high-PS treatment efficacy of SapC-DOPS and anti-PS targeted drugs.

Cancer cells that have higher surface PS exposure are more sensitive to SapC-DOPS treatment. Our previous data also suggest that cancer cells which have low PS exposure are more sensitive to radiation or chemotherapies, such as gemcitabine. The present invention has found that low-DC electric field mediated PS exposure decrease on GBM cells sensitize the cells to low-PS treatments such as chemotherapy (through the use of chemotherapy agents) and radiation. On the other hand, increasing GBM cells' PS exposure by different LIDC-EF enhances the high-PS treatment efficacy SapC-DOPS and anti-PS targeted drugs. A model of this concept is shown in FIG. 8. For the purposes of the present invention, the term "chemotherapy agents" is intended to mean any chemical substance of which the objective is to treat cancer by means of a general action aimed at affecting cell division, in particular by interacting with the essential structures of cell division and survival.

Examples of chemotherapy agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination.

Figure 9A:
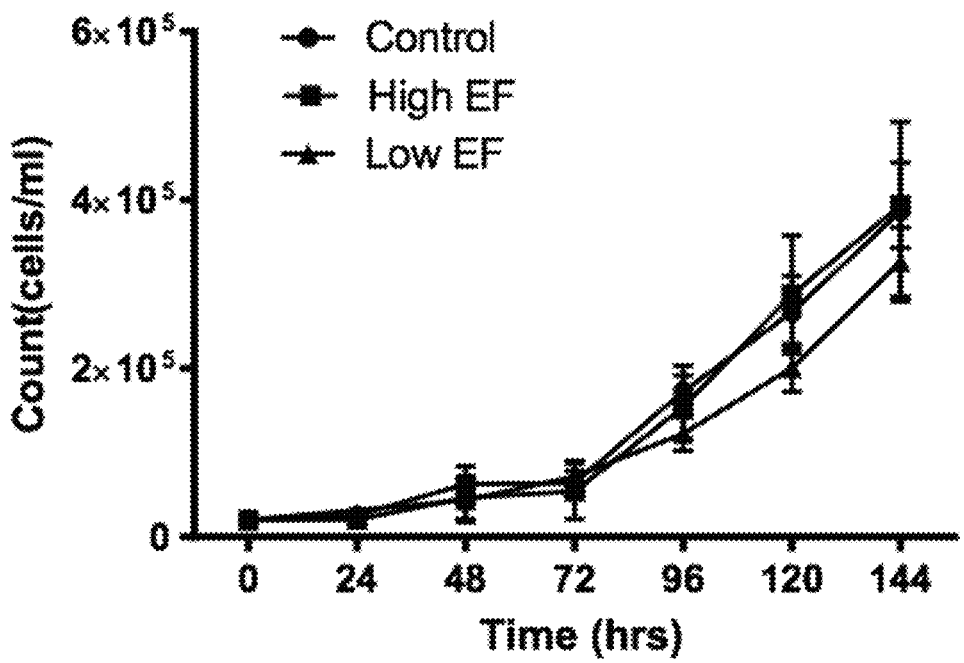
FIG. 9A is growth curve of U87ΔEGFR-Luc under high and low-DC Electric Field.
Figure 9B:
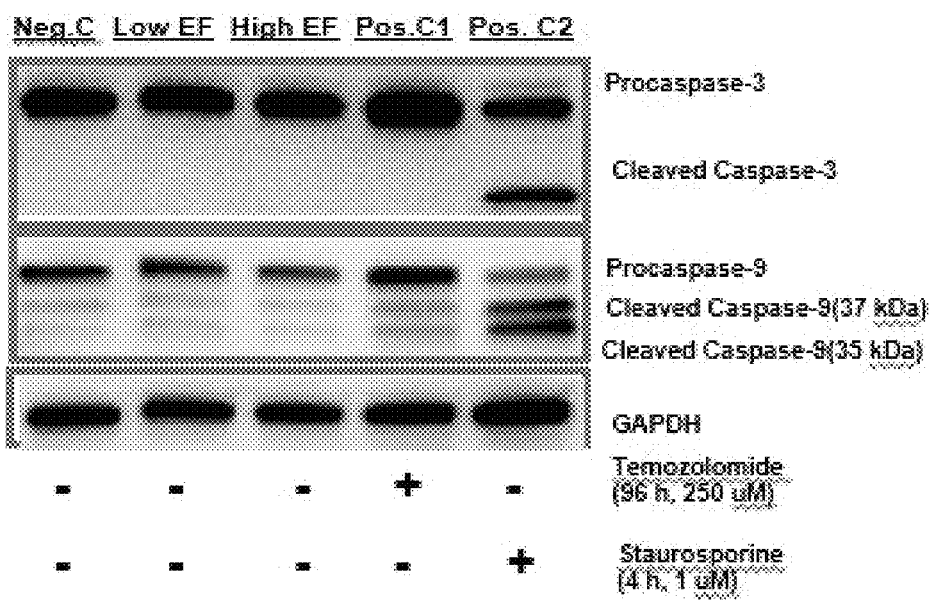
FIG. 9B is an image of a western blot showing the apoptosis induction of high and low EF applied U87ΔEGFR-Luc GBM cells.
Figure 9C:
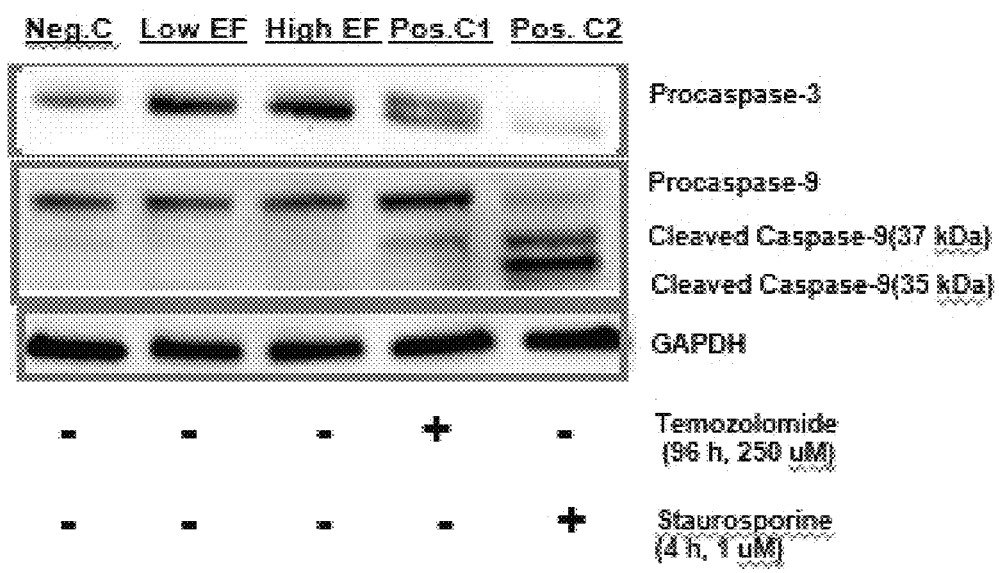
FIG. 9C is an image of a western blot showing the apoptosis induction of high and low EF applied astrocytes.

Referring to FIGS. 9A to 9C, the electric fields that we have applied were shown to not have a significant effect on cell growth. The results showed that high and low-EF didn't cause significant cell death in U87ΔEGFR-Luc GBM cells (FIG. 9A). Further, we confirmed that EF didn't induce the apoptosis in both U87ΔEGFR-Luc GBM cells and astrocytes (FIGS. 9B and 9C). These data suggest that EF induced PS exposure is not due to the apoptosis or necrosis.

Figure 10A:
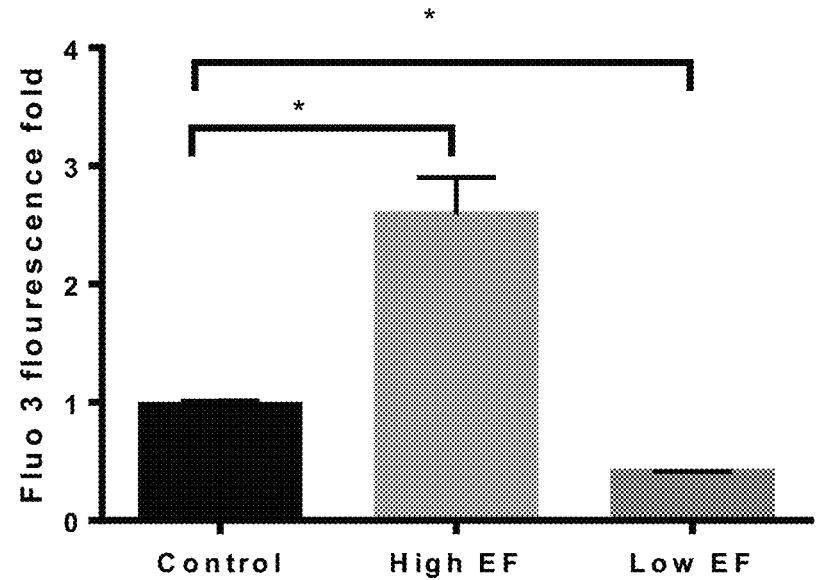
FIG. 10A is a graph showing the intracellular calcium concentration fold change comparison for control (No-EF), high EF, and low EF applied U87ΔEGFR-Luc GBM cells.
Figure 10B:
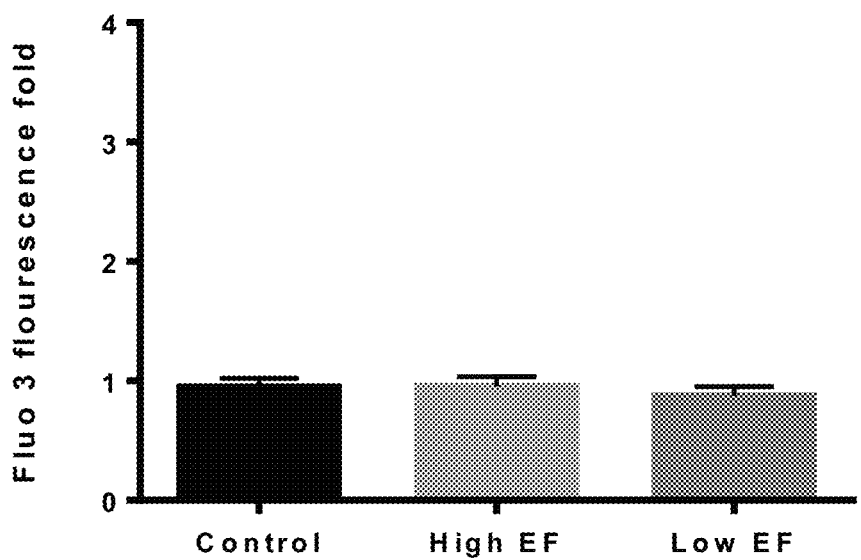
FIG. 10B is a graph showing the intracellular calcium concentration fold change comparison for control (No-EF), high EF, and low EF applied astrocytes cells.

The mechanism regarding PS regulation in electric field applied GBM cells was further considered. We have seen that there is a significant increase at the intracellular calcium concentration in high EF applied GBM cells. On the other hand, there is a dramatic decrease at the intracellular calcium concentration in the low EF treated GBM cells. These data suggest that EF induced PS externalization is controlled by a calcium dependent pathway. Without being bound by theory, we believe that EF regulates PS exposure in U87ΔEGFR-Luc GBM cells via activating or inactivating voltage gated calcium channel. Also, the PS exposure behavior that we observed is correlated with intracellular calcium concentration fold change. We further investigated the role of voltage gated calcium channel on EF induced PS exposure. We did not see a change at the intracellular calcium concentration in the high and low EF applied normal cells (FIG. 10).

Phosphatidylserine

The knowledge of membrane lipid function is relatively limited, as compared to protein or DNA function, due to the high complexity of the lipid structure/organization. While proteins are synthesized with only 20 different amino acids and nucleic acids are created with only four distinctive bases, cell membranes contain thousands of different lipids including phospholipids, lysophospholipids, sphingolipids, isoprenoids, glycolipids, free fatty acids (FFAs), ceramides, triglycerides, cholesterol and cholesterol esters.

Importantly, fundamental differences between the cell membrane compositions of normal and cancer cells enables the development of cell membrane-targeted cancer therapies. Normal cells usually have more neutrally charged phospholipids, such as sphingomyelin and phosphatidylcholine on the outer membrane surface, while PS and phosphatidylethanolamine (PE) are located in the inner membrane surface. Unlike normal cells, cancer cells and apoptotic cells lose their membrane PS asymmetry, leading to exposure of PS on the outer cell membrane leaflet (see FIG. 1). The cell membrane's asymmetrical distribution of phospholipids is regulated by P-type ATPases and aminophospholipid translocases (Flippases), which are regulated by ATP and/or calcium levels and transport PS to the inner membrane leaflet. When ATP is low or intracellular calcium is high, flippases are inactivated and PS accumulates on the outer membrane.

PS is an important membrane phospholipid that is synthesized by both eukaryotic and prokaryotic cells, and accounts for 3-10% of all cellular lipids. It is also highly concentrated in brain tissue where it constitutes 10 to 20% of total phospholipids. PS plays important roles in cellular functions including mitochondrial membrane integrity, release of presynaptic neurotransmitter, activity of postsynaptic receptor and protein kinase C activation in memory formation. Under healthy conditions in normal cells, PS is mostly located within the inner leaflet of the plasma membrane. However, in apotoptotic cells and cancer cells, flippase activity is diminished and PS accumulates on the cell surface. The extent of PS exposure on the outer cell membrane differs significantly between different types of cancers, and this variability is seen even within the same cancer type.

Evidence suggests that in addition to its role as a biomarker for cancer, PS contributes to many vital pathophysiological cellular processes. It has been shown that redistribution and translocation of PS takes place during a number of distinct biological events: (1) cell stress and injury, (2) cell death (for which PS exposure to the extracellular environment becomes a molecular marker and signals phagocytes to engulf the dying cell), and (3) infectious diseases (infection of virus, bacteria and protozoan parasites cause PS externalization). Table 1 lists the role of PS in a number of different diseases.

TABLE 1

| Disease | PS Involvement | Mechanism/Result |
| --- | --- | --- |
| Sickle cell disease | Surface PS increase | Spectrin cytoskeleton distruption, ATP depletion, decrease in intracellular magnesium, a rise in intracellular calcium, activation of protein kinase C (PKC). Increased membrane permeability to calcium→PS exposure |
| Viral infection | PS elevation in outer plasma membrane of cells | Increased PS synthesis at the ER and/or replication organelles.→PS exposure |
| Bacterial Infection | PS elevation in outer plasma membrane of cells | Increased intracellular calcium increase due to membrane leakage caused by bacterial toxins.→PS exposure |
| Scott Syndrome | Defective PS in membrane | Distrupted interaction of coagulation factors and blood cell membranes |
| Cancer (multidrug resistance) | Alteration in the level of surface PS | Reduced drug uptake, protein MDR1 Pgp on the cell membrane surface and facilitated drug removal from cancer cells→Drug resistance |
| Neurodegenerative Diseases | Increasing PS shows the state of disease | Apoptosis→PS exposure (early stage of disease) or necrosis (late stage of disease) |
| Aging and Alzheimer Disease | Decrease in the ratio of PS to cholesterol within neuronal membranes | Increased viscosity of cellular membranes, thus leads to reduced enzymatic activities, receptor functions, membrane carriers, and neuronal electrical characteristics→Loss of cell functions |

The diversity in its biological roles enables PS to represent a distinct therapeutic and imaging molecular target compared to other phospholipids and aminophospholipids. Therefore, PS is a molecule of substantial interest in several clinical disciplines. In particular, it has shown promise in the advancement of non-invasive imaging technology to help diagnosis and development of treatment efficacy for cancer and cardiovascular disease.

PS-Targeting Drugs

Saposin C (SapC) and dioleoylphosphatidylserine (DOPS) (SapC-DOPS), a nanovesicle, Bavituximab, a monoclonal antibody that recognizes PS, and PPS1D1, a PS-binding peptide-peptoid hybrid are three clinical PS targeting agents used for cancer localization and treatment.

SapC is an endogenous sphingolipid activator protein that plays a crucial role in lysosomal enzyme activation and sphingosine and ceramide production from sphingolipid degradation. Sap-C has strong binding affinity for PS at low pH, which provides a rationale for its selectivity since many solid tumors have acidic microenvironments due to lactate secretion from Warburg metabolism. At approximately 200 nm in diameter, the formulated SapC-DOPS nanovesicles selectively target and kill a variety of cancer cells including glioblastoma, pediatric tumor (nueroblastoma and peripheral nerve sheath tumor) and cancers of the pancreas, lung, and skin. SapC-DOPS induces cancer cell apoptosis and lysosomal cell death. SapC-DOPS has shown an exemplary safety profile and preliminary efficacy for glioblastoma and appendiceal carcinoma.

Bavituximab is a chimeric monoclonal antibody that binds to PS and activates a T-cell driven immune pathway while also blocking the PS immunosuppressive signaling of tumor cells. Bavituximab binds Fc gamma receptors on myeloid-derived suppressor cells (MDSCs), M2 macrophages and immature dendritic cells which leads to increased production of TNFα and IL-12 immunostimulatory cytokines. Consequently, it induces MDSC differentiation into M1-like dendritic cells and macrophages that cause induction of cytotoxic T lymphocytes. Bavituximab has been used with paclitaxel as an adjuvant therapy for the treatment of HER2-negative breast cancer in a phase I clinical trial. Treatment was well tolerated and resulted in an overall response rate of 85%. Recently, efficacy of Bavituximab has been assessed in a phase III clinical trial for advanced stage lung cancer. Unfortunately, there is no significant difference in the overall survival between Bavituximab in combination with docetaxel and docetaxel alone in patients with advanced, previously treated non-small cell lung cancer (NSCLC), and the addition of Bavituximab does not significantly minimize systemic side-effects. However, Bavituximab increased overall survival in patients pretreated with immune checkpoint inhibitors as compared to placebo-treated patients.

PS is specifically recognized by PPS1D1, a dimeric form of a peptide-peptoid hybrid. The monomer form of PPS1D1, PPS1, is composed of positively charged and hydrophobic residues. The PPS1 monomer is inactive, however PPS1D1 displays significant antitumor activity against lung cancer both in vitro and in vivo. Moreover, PPS1D1 significantly improved the therapeutic efficacy of docetaxel in lung cancer.

Binding of externalized PS activates tumor associated macrophage (TAM) receptor tyrosine kinases—Axl, Tyro3 and Mertk—and their ligand signaling in many ways. One process is apoptotic cell phagocytosis by macrophages and other phagocytes. It has also been shown that living cells under stress may have elevated surface PS, which leads to their phagocytosis via TAM-dependent mechanisms. In normal cells, externalized PS triggers regular TAM-mediated phagocytic events, such as retinal pigment epithelial cells phagocytosis in the eye. PS also plays an important role in the process of infection of a cell by enveloped viruses such as HIV, Ebola, dengue, vaccinia and Zika virus. Once these viruses are released from the host cells, their membrane envelopes contain huge amounts of externalized PS. If these PS-exposed cells encounter TAM receptor-expressing cells, they can dock via the macrophage TAM receptor which activates TAM receptor signaling to both promote endocytic engulfment of the virus and to inhibit the immune response to the virus. This process is called viral infection by 'apoptotic mimicry'.

PS exposure on the outer surface of cells can also serve as a marker for blood cell diseases. PS externalization occurs in red blood cells of patients suffering from thalassemia and sickle cell disease. The mechanisms responsible for PS externalization in these diseases is still unclear, with the possibilities including disorganization of spectrin-like cytoskeleton, shortage of cellular ATP, decrease in intracellular magnesium, increase in intracellular calcium, activation of protein kinase C (PKC) for sickle cell diseases, or membrane oxidization derived from the commonly observed iron overload in thalassemia patients. It has also been shown that the level of PS on the outer surface of these cells increases in other blood diseases, such as stomatocytosis, uremia, malaria and hyperbilirubinemia.

Altering the Surface PS to Increase the Efficacy of PS Targeting Modalities

Cancer cells that have higher surface PS exposure are more sensitive to SapC-DOPS treatment. Cancer cells which have low PS exposure are more sensitive to radiation or chemotherapies, such as gemcitabine. Importantly, our results indicate that altering the level of PS exposure in cancer cells will sensitize cancer cells to PS targeting drugs such as SapC-DOPS and gemcitabine. SapC-DOPS combined with temozolomide has a strong synergistic effect compared with temozolomide alone in glioblastoma (GBM). While not being bound by theory, the potential mechanism may be that temozolomide increases tumor PS exposure via induction of apoptosis, thereby GBM cells become much more sensitive to the cytotoxic effect of SapC-DOPS. An alternative explanation is that since there is a range of surface PS even within a specific cell line, radiation and chemotherapy kill the low surface PS cells and leave the higher surface PS cells (thus increasing the mean surface PS values) that SapC-DOPS can then target.

Phosphatidylserine as a Tumor Imaging Target

PS exposure level in tumors is a potential predictor of successful therapy. Monitoring levels of exposed PS is a compelling approach to detect tumors, because many treatment options, including radiotherapy and chemotherapy, increase membrane PS exposure on tumor endothelium and tumor cells. Successful PS-targeted cancer cell imaging has been demonstrated by several groups using different carriers. Table 2 describes several PS-targeted imaging modalities.

TABLE 2

| | PS-targeted Therapy | | |
|---|---|---|---|
| Type | PS-targeting drugs or antibody | Mechanism | Cancer Type(s) |
| Proteoliposomal nanovesicles | SapC-DOPS (Phase I clinical trial) | Caspase-mediated apoptosis | Pancreatic Cancer Glioblastoma Lung Cancer |
| Monoclonal antibody | Bavituximab (Phase III clinical trial) | Activation of T-cell-driven adaptive immune pathway via M1-TAMs | Prostate cancer Non-small cell lung cancer |
| Peptide-peptoid hybrid | PPS1D1 | Membrane disruption | Lung cancer |

TABLE 2-continued

PS-targeted Imaging

| Type of imaging modality | PS-targeting antibody + imaging compound | Detailed Description | Cancer Type(s) |
|---|---|---|---|
| Positron Emission Tomography | PGN635 + $^{89}$Zr | High accumulation of $^{89}$Zr-PGN635 in apoptosis-induced tumor site. | Human colorectal cancer Breast cancer |
| MRI (9.4 T) | PGN635 + Superparamagnetic iron oxidenanoparticles (SPIO) | Drastic reduction on T2-weighted MRI signal intensity. | Breast cancer |
| MRI (7 T) | SapC DOPS + Gadolinium | Increased R1 relaxation rate and enhanced T1-weighted MRI was observed. | Glioblastoma |
| Dual Imaging (Optical/Positron Emission Tomography) | SapC-DOPS + Iodine-127($^{127}$I)/Iodine 125($^{125}$I) + phenol-substituted dye | Higher cellular uptake of $^{125}$I-labeled nanovesicles in glioblastoma as compared with sham brains (4.8 fold higher). | Glioblastoma |

Combinational PS-targeted Therapy

| Modality | PS-targeting antibody + chemo/radiation | Detailed Description | Cancer Type(s) |
|---|---|---|---|
| PS-targeting antibody + chemotherapy | 3G4 + Gemcitabine | Significant reduction of primary tumor growth and metastatic burden. Higher macrophage infiltration in tumor site as compared with control (14-fold higher). | Pancreatic cancer |
| PS-targeting antibody + radiation | 2aG4 + Radiation | Reduction in tumor vascularity in the tumor treated with 2aG4 + radiation therapy (91% decrease). Enhanced monocyte/macrophage infiltration into the tumor mass. | Lung cancer |
| PS-targeting antibody + immune activators and checkpoint inhibitors | mch1N11 + anti-PD-1 or anti CTLA-4 | Elevated IL-2, IFN-γ, and TNF-α secretion and higher ratio of CD8$^+$ Tcells to MDSC and Tregs in treated tumor cells. | Breast cancer Melanoma tumors |

Contrast agent-loaded SapC-DOPS nanovesicles can be used to monitor and trace different cancer cell lines. Due to the fact that tumors express abundant PS on the cell surface and have a lower extracellular pH (pH ~6) than normal tissues (pH ~7), the SapC-PS interaction provides a valuable system for targeted tumor imaging and therapy. Successful targeting of cancer cells with SapC-DOPS using PS has been reported using optical, magnetic resonance imaging (MRI), as well as Single-Photon Emission Computed Tomography (SPECT).

Figure 3:
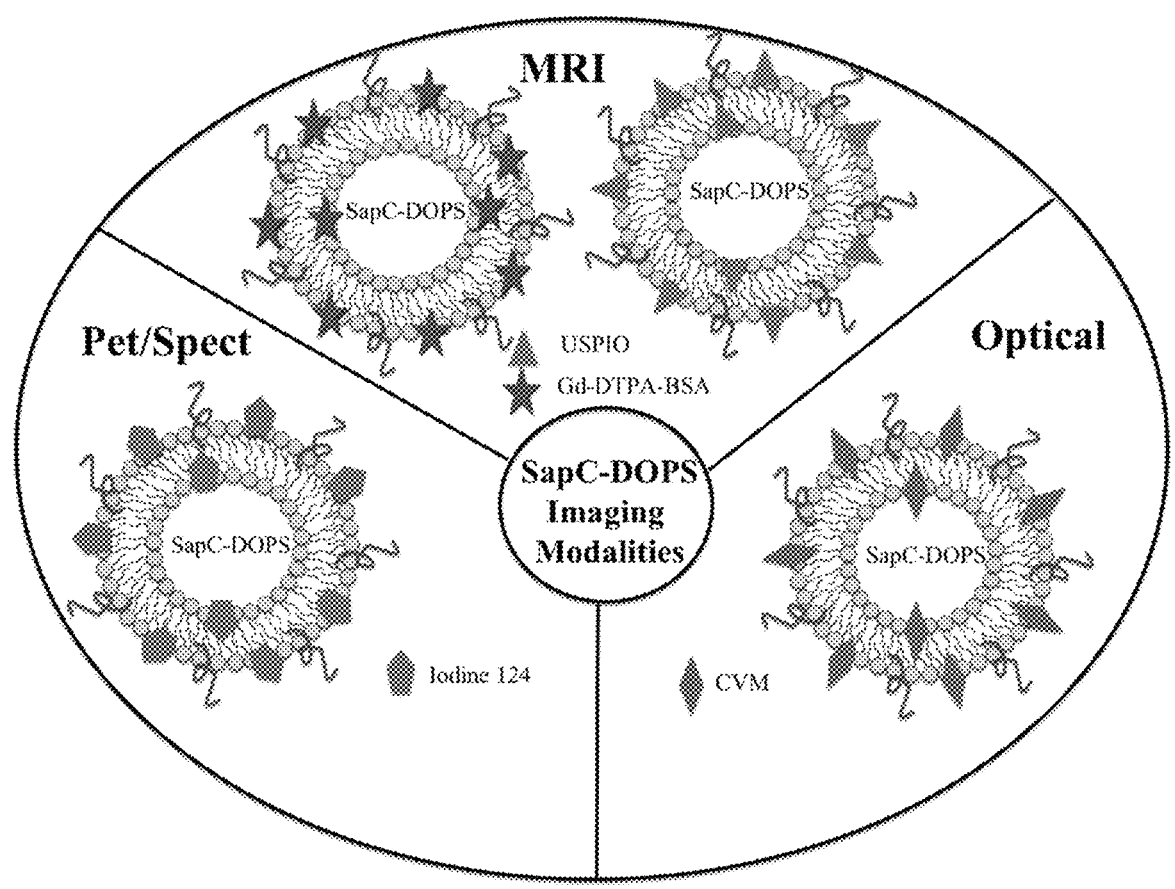
FIG. 3 is a schematic representation of SapC-DOPS based tumor imaging modalities.

FIG. 3 is a schematic representation of SapC-DOPS based tumor imaging modalities. For in vivo optical images, SapC-DOPS nanovesicules can be labeled with far red fluorophore, CellVue Maroon (CVM) for optical imaging. For in vivo MRI imaging, ultra-small cuperparamagnetic iron oxide (USPIO) or gadolinium chelates (Gd-DTAP-BSA) can be encapsulated into SapC-DOPS nanovesicles and used as MRI contrast agents. For in vivo Pet/Spect imaging, SapC-DOPS can be combined with Iodine-124 as a contrast agent.

PS is one of the most remarkable and prevalent fingerprints of cells in cancer and some other diseases. Hence, it is an attractive target for treatment and imaging. Most importantly, although different biomarkers have been reported for different cancer cells types, PS is a ubiquitous biomarker and can be used to target most cancers. SapC-DOPS and Bavituximab are two PS targeting drugs that are currently being investigated in cancer clinical trials. A combination of PS-targeting therapies with current treatment modalities such as chemotherapy, radiation, and immune checkpoint inhibitors (including antibodies targeting CTLA-4, PD-1, and PD-L1) has the potential to treat a wide variety of cancers. Current PS targeted imaging modalities, such as optical imaging, MRI and PET/SPECT enable us to selectively image tumors and certain other types of diseases.

Due to the fact that tumors express abundant PS on the cell surface and have a lower extracellular pH (pH ~6) than normal tissues (pH ~7), the SapC-PS interaction provides a valuable system for targeted tumor imaging and therapy. Targeting of cancer cells with SapC-DOPS using PS has been successful using optical, magnetic resonance imaging (MRI), and single photon emission computed tomography (SPECT). The present invention can be used to enhance the efficacy of PS targeted imaging. In addition, the imaging technique of present invention allows for the detection of cancer in the early stage.

Electric Field

Figure 2:
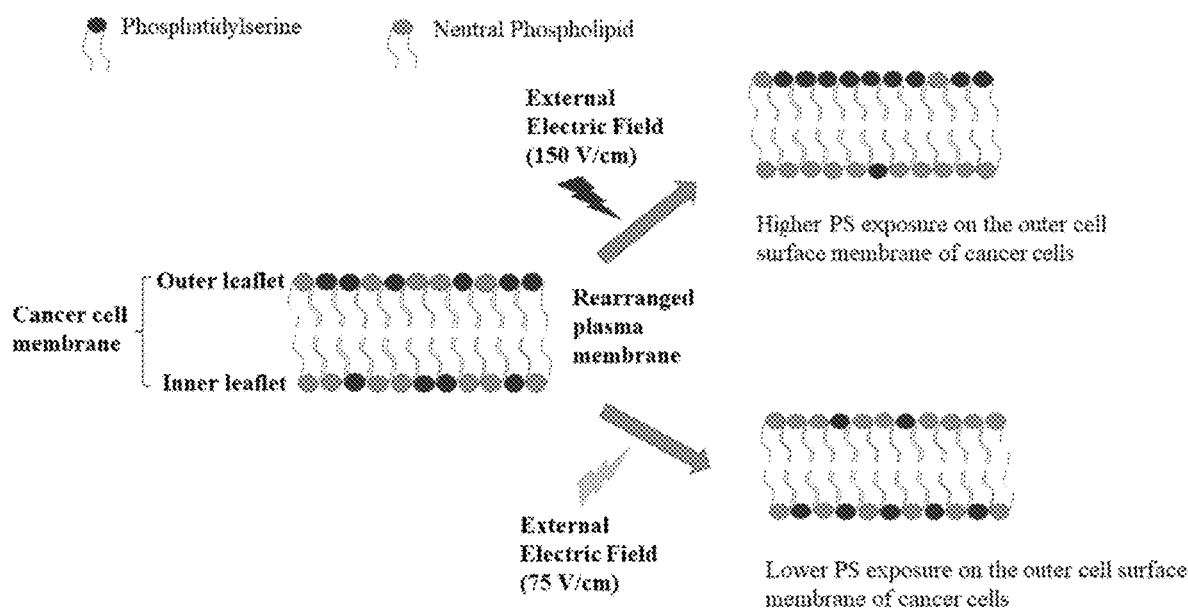
FIG. 2 is a schematic representation of PS modulation in cancer cells via external electric field.

Therapeutic application of electric field is gaining interest in the fight against cancer. Tumor treating field (TTField), a low intensity electric field, was approved in 2011 by the FDA for treatment of glioblastoma. It has lower toxicity and fewer side effects when compared to chemotherapy. We have found that applying direct current (DC) electric fields (DC-EFs) with different magnitudes (75-150 V/cm) can modulate cell surface PS exposure level in U87ΔEGFR-Luc glioblastoma cells (FIG. 2). These data indicate that external DC-EFs are a novel platform for enhancement of GBM treatment efficacy. FIG. 2 is a schematic representation of PS modulation in cancer cells via external electric field.

Optical Imaging

Optical imaging is commonly used in preclinical cancer research since it is cost effective, easy-to-use, and provides real-time results. In particular, it is employed to study drug pharmacokinetics, cancer specific markers, and to monitor the effects of drugs in small animals.

Previous studies showed that SapC-DOPS can selectively target tumor cells. It has been demonstrated that CellVue Maroon (CVM), a far red fluorophore-tagged SapC-DOPS nanovesicles, can be utilized for in vivo optical imaging of brain tumors and arthritic joints. A rotational bed can be used to obtain the multi-angle rotational optical image. It has been confirmed that optical imaging intensity depends on the optical imaging angle, which has been shown to vary with cancer type in different animal models. For example, the optical imaging angle is determined as 100 and 200 for orthotopic and mut49 tumor bearing mouse models, respectively. It has also been shown that SapC-DOPS nanovesicle-based optical imaging not only provided information about the arthritis or cancer site, it also enabled assessment of disease or cancer state/progression. Similar results have been shown in pancreatic tumors and neuroblastoma. However, while optical imaging is highly sensitive, it is not widely used in humans because of the limited fluorescent signal detection in deep tissues and the autofluorescence effect. It has been demonstrated that phenol-substituted membrane-intercalating lipophilic dyes and iodinated lipophilic dyes can be combined with SapC-DOPS. This allows dual imaging of glioblastoma (optical and PET imaging).

PET/SPECT Imaging

Both positron emission tomography (PET) and single-photon emission computed tomography (SPECT) are nuclear medicine imaging techniques. The procedure includes the administration of radioactive tracers to patients and detection of gamma ray emissions from the tracers. Since the PET and SPECT imaging have high sensitivity and promise for clinical applicability, the development of radiotracers for cancer imaging has attracted significant interest.

It has been reported to use phenol-substituted membrane intercalating lipophilic dyes to label SapC-DOPS with iodine-124 for PET imaging. The results show that 125I-labeled nanovesicles are absorbed 4-8 times higher in glioblastoma than sham brains with a very low thyroid uptake. These results suggested selective tumor targeting and minimal reporter degradation in blood. Further, Bavituximab and PGN635 (1N11) have been used as imaging agents in preclinical research. In animal studies, 74As-labeled bavituximab was successfully used to image tumors in the R3227-AT1 rat Dunning prostate model.8589 Zr-labelled PGN635 was evaluated by positron emission tomography (PET) imaging in mouse tumor xenograft models. A high accumulation of 89Zr-PGN635 was seen in treated tumors undergoing apoptosis (tumor to blood ratio is 13).

EXAMPLES

Example 1

SapC-DOPS nanovesicles were synthesized as follows: Recombinant human SapC was expressed in *Escherichia coli*. Purified SapC was then mixed with dioleoylphosphatidylserine in acidic buffer (citrate/phosphate buffer, pH 5). The protein-lipid mixture was sonicated at 4° C. then ultracentrifuged to produce SapC-DOPS nanovesicles. There was no detectable SapC in the supernatant fraction, indicating a very high loading/coupling efficiency. The sonicated SapC-DOPS complexes contain monodispersed, unilamellar vesicles with a mean diameter of ~200 nm.

To produce a probe for MRI, iron oxide (IO) particles (ferumoxtran-10; ~20 nm in diameter) were encapsulated into SapC-DOPS nanovesicles. The dextran coating was oxidized on the IO particles to create aldehyde groups. The oxidized IO particles were then mixed with SapC and lipids to generate SapC-DOPS-IO nanovesicles. Surface aldehydes of the IO particles form covalent Schiff bonds at high pH with amines of DOPS. The vesicles were formed by extrusion through a 200-nm polycarbonate membrane. The unencapsulated IO particles were removed through a Con-A Sepharose 4B column. The SapC-DOPS-IO nanovesicles were stabilized in 4-(2-hydroxyethyl)-1-piperazine ethanesulfonic acid (HEPES), buffered to pH 8.

Example 2

Magnetic resonance imaging (MRI) is a widely used imaging technique for clinical disease diagnosis. It has a high spatial resolution and an excellent soft tissue contrast. Vesicles useful in the present invention were labeled with ultra-small superparamagnetic iron oxide (USPIO) particles. The labelled vesicles enabled tumor selective imaging of neuroblastoma via MRI both in vitro and in vivo. According to the in vitro results, compared to control cells (7.84 s−1, 11.04 s−1) there was a significant increase on the R2 and R2* relaxation rates (14.64 s−1, 26.74 s−1) when the cells were treated with SapC-DOPS-IO for 24 h. According to the in vivo study conducted in mice, T2*-weighted imaging at 7 T showed that the signal intensity in tumors dropped immediately after injection of SapC-DOPS-IO and gradually declined further before rebounding slightly 24 h later. The signal intensity drop was observed over the entire tumor. Inductively coupled plasma atomic emission spectroscopy (ICP-AES) analysis showed that the concentration of iron in the tumor of a mouse injected with SapC-DOPS-IO is approximately five-fold higher than the concentration of iron in the tumor of a free O-treated mouse.

Example 3

Figure 4A:
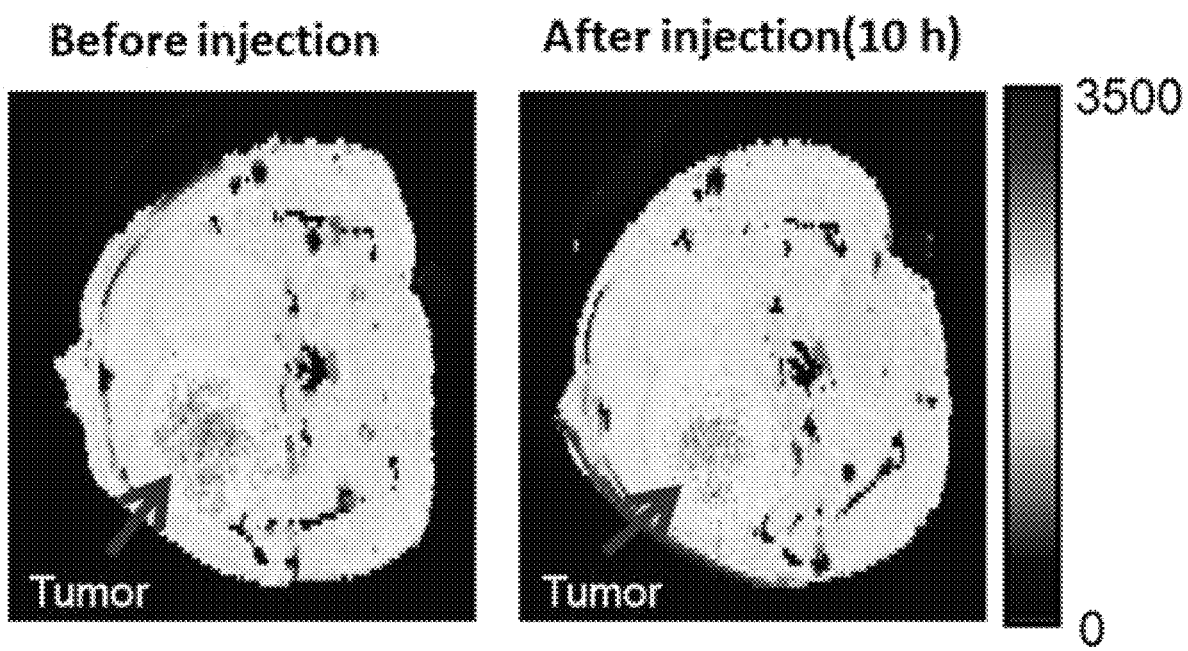
FIG. 4A is a high resolution MRI of a glioma in a mouse brain.
Figure 4B:
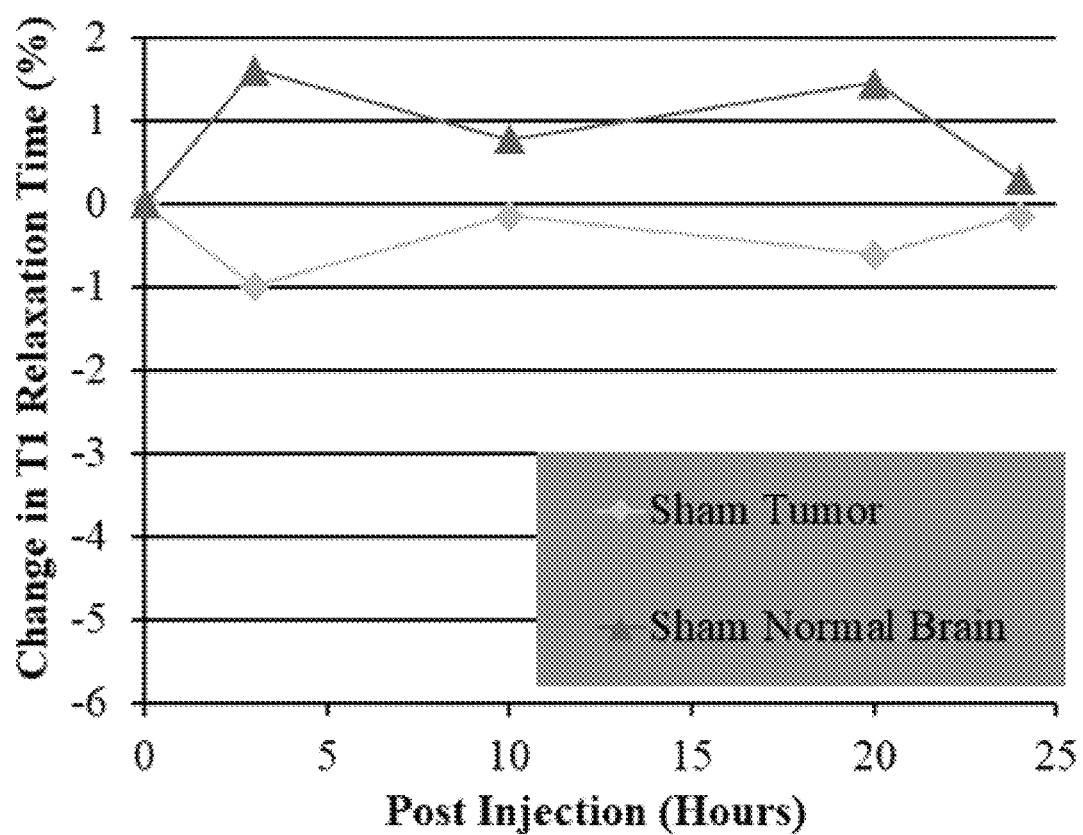
FIG. 4B is a graph showing the percent change in T1 after SapC-DOPS vesicle injection in the sham tumor and sham normal brain.
Figure 4C:
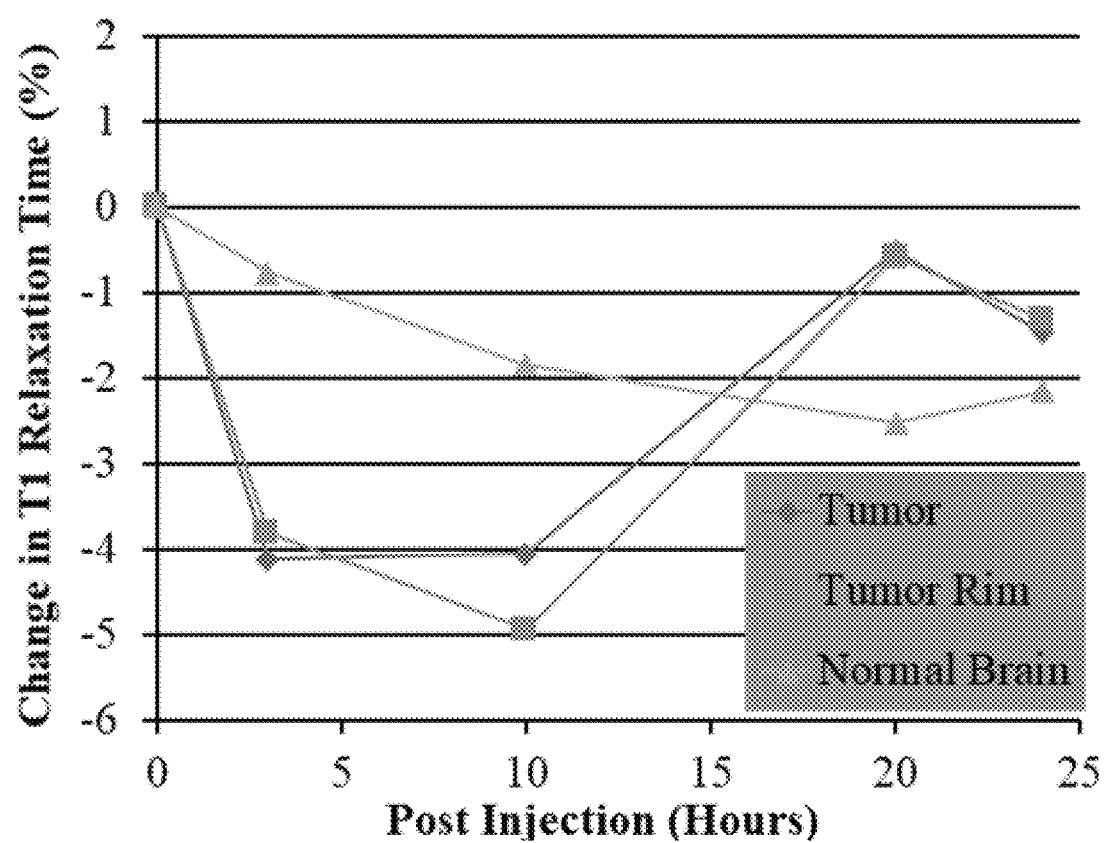
FIG. 4C is a graph showing the percent change in T1 after injection of Gd-DTPA-BSA/SapC-DOPS vesicle in the tumor ("Tumor"), tumor rim cells ("Tumor Rim") and normal brain ("Normal brain").

The use of a paramagnetic gadolinium chelate-loaded SapC-DOPS (Gd-DTPA-BSA/SapC-DOPS) vesicles as a targeted contrast agent for imaging glioblastoma multiforme tumors are also useful in the present invention. Gd-DTPA- BSA/SapC-DOPS vesicles and Gd-DTPA display a similar relaxivity of 3.32 and 2.80 (s·mM)−1, respectively, at 7 T. According to the in vivo experiments, the R1 values of the tumor before injection of Gd-DTPA-BSA/SapC-DOPS vesicles, sham injected brain, and contralateral normal brain were 0.4676±0.010 s−1, 0.5216±0.034 s−1, and 0.5596±0.003 s−1, respectively. The mean change in the tumor R1 value at 10 h postinjection was 9.0±2.3%, whereas the sham injected brain and normal brain did not show any significant increase 1.4±1.9%, and 1.2±1.5%, p<0.05. At 24 h postinjection, the tumor R1 remained elevated (7.9±1.5%, P<0.05) compared with the normal and sham brains, but it was statistically similar to the controls (4.7±2.0%, p>0.05). FIG. 4A shows T1 maps of tumor cells before treatment and after 10 h treatment with Gd-DTPA-BSA/SapC-DOPS vesicles. The results show that there is a clear reduction in the T1 relaxation time 10 h after injection of Gd-DTPA-BSA/SapC-DOPS vesicles compared with before injection. FIG. 4B shows the percent change in T1 relaxation of sham tumor and sham normal brain treated with only SapC DOPS. At 4 h, 10 h, and 20 h, the increase in T1 relaxation time is higher in the sham normal brain compared with sham tumor. By 24 h postinjection, the T1-weighted signal is similar in both tissues. FIG. 4C shows the percent change in T1 relaxation after injection of Gd-DTPA-BSA/SapC-DOPS vesicle in the tumor, tumor rim cells, and normal brain. At 4 and 10 h postinjection, the T1 relaxation time change is higher in the tumor (4.12%, −4.05%) and tumor rim (−3.81%, −4.94%) compared with the normal brain (−0.76%, −1.84%).

FIG. 4A is a high resolution MRI of a glioma in a mouse brain. Tumor T1 relaxation time (s−1) maps before and 10 h after injection of Gd-DTPA-BSA/SapC-DOPS vesicles. FIG. 4B shows the percent change in T1 after SapC-DOPS vesicle injection in the sham tumor and sham normal brain. FIG. 4C shows the percent change in T1 after injection of Gd-DTPA-BSA/SapC-DOPS vesicle in the tumor ("Tumor"), tumor rim cells ("Tumor Rim") and normal brain ("Normal brain").

Example 4

Materials and Methods: A parallel-plate capacitor was used to apply an electric field to cells that were seeded on petri dishes. The calculated field intensities for the system were 750 mV mm−1 (low) or 1500 mV mm−1 (high). U87ΔEGFR-Luc cells (a glioblastoma cell line) were used as the testing cells and astrocytes were used as normal controls. The cells were exposed to EF for pre-determined time intervals and then stained with Annexin V-FITC using a standard protocol; surface PS levels were quantified using flow cytometry (BD-Fortessa). Results were analyzed using 2-Factor ANOVA with the Bonferroni post-hoc test (α=0.05). Intracellular calcium was measured by using Fluo-3 fluorescein dye (Invitrogen, Carlsbad, CA). A Caspase 3,9 assay with western blot was used to determine cell apoptosis. Cell viability was evaluated by counting the cells under an inverted microscope.

Figure 5A:
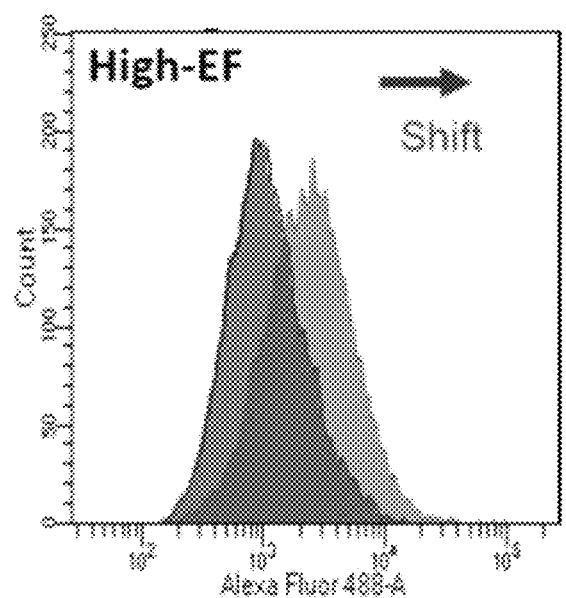
FIG. 5A is a graph showing the overlaid flow cytometry histograms of Annexin V-FITC of U87ΔEGFR-Luc cells in high-EF conditions at 0 hrs (blue) and 6 hrs (orange).
Figure 5B:
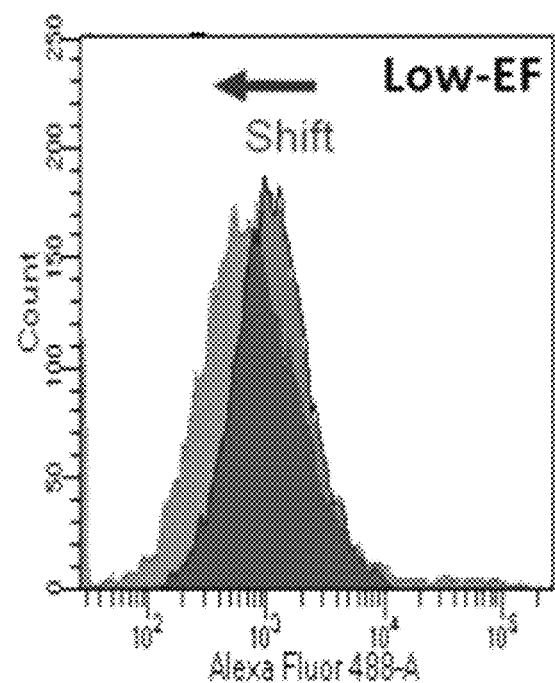
FIG. 5B is a graph showing the overlaid flow cytometry histograms of Annexin V-FITC of U87ΔEGFR-Luc cells in low-EF conditions at 0 hrs (blue) and 6 hrs (orange).

The results demonstrate differential effects on surface PS levels of U87ΔEGFR-Luc cells following exposure to low and high LIDC-EF. Exposure to low EF significantly reduces PS surface levels at the initial time points and up to 6 hrs (p<0.05) vs. baseline level. In contrast, exposure to high EF results in the significantly greater surface PS levels for the entire time period, up to 24 hrs (p<0.01), and was significantly larger than the low-field values (p<0.05). Flow cytometry histograms in FIG. 5A shows the shift in mean fluorescence intensity (MFI) of Annexin V-FITC after 6 h of the high EF exposure. FIG. 5b shows the shift in mean fluorescence intensity (MFI) of Annexin V-FITC after 6 h of the low EF exposure. On the other hand, the low and high-EF do not affect the PS exposure of normal cells. Intracellular calcium levels were 2.5 times higher after 6 h of the high EF exposure compared with control U87ΔEGFR-Luc cells. On the contrary, the intracellular calcium concentration was 2 times lower than untreated cells after 6 h of low EF. EF does not affect the intracellular calcium concentration in normal cells. Further, EF does not affect the viability of U87ΔEGFR-Luc cells.

The results demonstrate that the surface PS exposure level is altered by applying different electric fields. Our previous data show that the cancer cells, which generally have higher surface PS exposure than normal cells, are more sensitive to SapC-DOPS treatment. Interestingly, our data show that the cancer cells that have initially lower surface PS exposure are more sensitive to chemo treatment such as gemcitabine. Thus, combination of high EFs with SapC-DOPS or low EFs with temozolomide can be good candidates as novel GBM therapies with enhanced cytotoxicity and specificity but fewer side effects compared with current treatments.

Example 5

U87ΔEGFR-Luc cells were treated with hydroxyurea (HU) in complete medium to a final concentration of 4 mM for 24 h. Following synchronization treatment, cells were treated 6 hrs high EF whereas control cells were incubated with HU-free medium for 6 hrs. The resulting data showed that high electric field caused G1 to G2 phase transition (8.6% increase in G2 population and 11.1% in G1 population, see Table 3) in GBM cells. High surface phosphatidylserine (PS) cells are predominantly in the G2/M phase and SapC-DOPS preferentially targets high surface PS cells. These results show that high electric field can increase the surface PS of cancer cells by shifting the cell cycle phase from G1 to G2/M which will sensitize the cells to PS targeted drugs, such as SapC-DOPS nanovesicles (BXQ-350). Table 3 shows a comparison of cell cycle percentage of 6 h High EF treated cells and control cells.

TABLE 3

|  | G1 Phase(%) | S Phase(%) | G2/M Phase(%) |
|---|---|---|---|
| Control | 63.2 | 12.7 | 22.5 |
| High Electric Field | 52.1 | 14.6 | 31.1 |

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A method of treating cancer in a subject who is in need thereof, comprising applying one or more direct current electric fields (DC-EFs) to the subject and administering to said subject an additional treatment selected from the group consisting of Saposin C (SapC) and dioleoylphosphatidylserine (DOPS) (SapC-DOPS), anti-phosphatidylserine targeted drugs, and combinations thereof, wherein the magnitude of the applied DC-EF is from 100 V/cm to 1,500 V/cm.

2. The method of claim 1 wherein the magnitude of the applied DC-EF is 150 V/cm.

3. The method of claim 1 wherein the additional treatment comprises SapC-DOPS.

4. The method of claim 1 wherein the additional treatment comprises anti-phosphatidylserine targeted drugs.

5. The method of claim 4 wherein the anti-phosphatidylserine targeted drugs are selected from the group consisting of Bavituximab, PPS1D1 and combinations thereof.

6. A method of killing or inhibiting the growth of cancer cells in a target region, the method comprising the steps of:
   a. applying, to the target region, one or more direct current electric fields (DC-EFs), wherein the applied DC-EF has a magnitude from 100 V/cm to 1,500 V/cm; and
   b. treating the cancer cells with additional treatment selected from the group consisting of radiation, an effective amount of Saposin C (SapC) and dioleoylphosphatidylserine (DOPS) (SapC-DOPS), anti-phosphatidylserine targeted drugs, and combinations thereof.

7. The method of claim 6, wherein the applying step and the treating step are performed simultaneously.

8. The method of claim 6 wherein the additional treatment comprises SapC-DOPS.

9. The method of claim 6 wherein the additional treatment comprises anti-phosphatidylserine targeted drugs.

10. The method of claim 9 wherein the anti-phosphatidylserine targeted drugs are selected from the group consisting of Bavituximab, PPS1D1 and combinations thereof.

11. A method of imaging cancerous cells in a subject comprising:
   a. applying one or more direct current electric fields (DC-EFs) to the subject, wherein the magnitude of the applied DC-EF is from 100 V/cm to 1,500 V/cm;
   b. administering to said subject an additional treatment of SapC-DOPS, wherein the SapC-DOPS treatment comprises one or more contrast agents; and
   c. detecting the one or more contrast agents in the subject.

* * * * *